United States Patent
Hammer et al.

(10) Patent No.: US 10,729,067 B2
(45) Date of Patent: Aug. 4, 2020

(54) BIOMASS IMPACT SENSOR HAVING A CONFORMAL ENCASEMENT ENVELOPING A PRESSURE SENSITIVE FILM

(71) Applicant: Deere and Company, Moline, IL (US)

(72) Inventors: Curtis R. Hammer, Bettendorf, IA (US); Jonathan J. Nelson, Davenport, IA (US)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 16/166,100

(22) Filed: Oct. 20, 2018

(65) Prior Publication Data

US 2020/0120870 A1 Apr. 23, 2020

(51) Int. Cl.
| | |
|---|---|
| A01D 41/127 | (2006.01) |
| G01F 1/30 | (2006.01) |
| G01L 1/20 | (2006.01) |
| G01N 33/02 | (2006.01) |
| G01L 5/00 | (2006.01) |

(52) U.S. Cl.
CPC ............ *A01D 41/127* (2013.01); *G01F 1/30* (2013.01); *G01L 1/205* (2013.01); *G01L 5/0047* (2013.01); *G01N 33/025* (2013.01)

(58) Field of Classification Search
None
See application file for complete search history.

(56) References Cited

U.S. PATENT DOCUMENTS

| | | |
|---|---|---|
| 4,466,543 A | 8/1984 | Zwahlen et al. |
| 4,490,964 A | 1/1985 | Eldridge et al. |
| 6,053,045 A * | 4/2000 | Nakamura .......... G01P 15/0922 73/514.31 |
| 6,524,183 B1 | 2/2003 | Van Quekelberghe |
| 6,681,631 B2 * | 1/2004 | Apel ..................... G01H 11/08 73/514.34 |
| 6,698,272 B1 | 3/2004 | Aimirante |
| 7,705,437 B2 | 6/2010 | Barrera et al. |
| 2004/0161919 A1 | 8/2004 | Cha |
| 2006/0253942 A1 | 11/2006 | Barrera |

(Continued)

FOREIGN PATENT DOCUMENTS

| | | |
|---|---|---|
| CN | 106768569 A | 5/2017 |
| EP | 0339142 | 11/1989 |

(Continued)

OTHER PUBLICATIONS

Satu Rajala, Jukka Lekkala, PVDF and EMFi Sensor Materials—A Comparative Study, www.elsevier.com/locate/procedia, Sep. 5, 2010.

(Continued)

*Primary Examiner* — Harshad R Patel

(74) *Attorney, Agent, or Firm* — Rathe Lindenbaum LLP

(57) ABSTRACT

A biomass impact sensor for sensing impacts of biomass material may include a pressure sensitive film having a first sensing face and a second opposite face, a first layer of a first material composition directly abutting the first sensing face having a first stiffness, and a second layer of a second material composition directly abutting the second opposite face. The first layer and the second layer may be joined along opposite edges of the pressure sensitive film to envelope the sensing material layer on the opposite edges.

20 Claims, 3 Drawing Sheets

(56) References Cited

U.S. PATENT DOCUMENTS

| | | |
|---|---|---|
| 2009/0075429 A1 | 3/2009 | Sato |
| 2012/0055257 A1 | 3/2012 | Shaw-Klein |
| 2012/0062245 A1 | 3/2012 | Bao et al. |
| 2013/0111971 A1 | 5/2013 | Pudas |
| 2013/0125652 A1* | 5/2013 | Kim ................. G01P 15/09 73/514.34 |
| 2016/0025531 A1* | 1/2016 | Bischoff ............ G01L 1/146 73/861.73 |
| 2017/0372853 A1 | 12/2017 | Taniguchi |

FOREIGN PATENT DOCUMENTS

| | | |
|---|---|---|
| EP | 0872719 | 10/1998 |
| GB | 1514274 | 6/1978 |
| GB | 2558899 A | 7/2018 |

OTHER PUBLICATIONS

European Search Report for App 15176406.5 dated Feb. 8, 2017.
Alexander Horoschenkoff and Christian Christner, Carbon Fibre Sensor: Theory and Application, Chapter 0, Aug. 22, 2012.
Jiaojiao Xu, Yaoming Li, A PVDF Sensor for Monitoring Grain Loss in Combine Harvester, Key Laboratory of Modern Agricultural Equipment and Technology Jiangsu University, P.R. China 2013.
European Search Report issued in counterpart European Patent Application No. 19203895.8 dated Mar. 11, 2020 (7 pages).

* cited by examiner

BIOMASS IMPACT SENSOR HAVING A CONFORMAL ENCASEMENT ENVELOPING A PRESSURE SENSITIVE FILM

CROSS-REFERENCE TO RELATED PATENT APPLICATIONS

The present application is related to co-pending U.S. patent application Ser. No. 14/794,089 filed on Jul. 8, 2015 by Lutz Bischoff et al. and entitled PARTICULATE MATTER IMPACT SENSOR, the full disclosure of which is hereby incorporated by reference.

BACKGROUND

Biomass impact sensors sense the quantity or percentage of biomass in a stream of material. Biomass impact sensors make such determinations based upon impacts of the biomass material, such as grain or material other than grain, against a sensing face or surface. Such biomass impact centers may be employed in harvesters to detect grain yield, grain loss and/or material other than grain.

Figure 1:
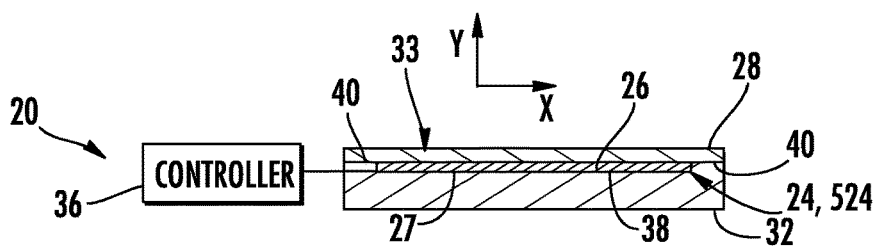
FIG. 1 is a sectional view of an example biomass impact sensor.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed are example biomass or particulate matter impact sensors that provide enhanced accuracy and resolution in a package that may be manufactured with less complexity and at a lower cost. The example biomass or particulate matter impact sensors sandwich a pressure sensitive film or layer between two other portions of an encasement that have different degrees of stiffness, wherein the two portions of the encasement conform to the shape of the film while being coupled or joined to one another outwardly beyond and alongside opposite edges of the pressure sensitive film. As a result, the pressure sensitive film may be completely contained and housed in an encasement that fully supports the pressure sensitive film on both opposite faces of the pressure sensitive film, securely holding and retaining the pressure sensitive film in place. This encasement further facilitates simplified and cost-effective manufacture.

The differences in the stiffnesses between the first and second portions of the encasement enhance sensing performance of the film. The stiffer front portion effectively transmits forces from biomass impact or particulate matter impact to the sensing face of the film. The less stiff rear portion of the encasement absorbs the forces of such impacts after they have been detected so as to reduce the possibility of the pressure sensitive film shattering, cracking or otherwise becoming damaged.

In one implementation, the pressure sensitive film is completely encapsulated, surrounded on all sides and faces to provide a secure and durable environment for the pressure sensitive film, facilitating use of the biomass impact sensor in rough and dirty environments. As a result of the above noted achievements, the example biomass impact sensors disclosed herein are well suited for use in rough and dirty environments, such as when sensing biomass material in a harvester.

Disclosed herein is an example biomass impact sensor for sensing impacts of biomass material that comprises a pressure sensitive film having a first sensing face and a second opposite face, and a conformal encasement enveloping the pressure sensitive film so as to directly abut the first sensing face and the second opposite face. The conformal encasement may comprise a first portion adjacent the first sensing face having a first stiffness, a second portion adjacent the second opposite face having a second stiffness less than the first stiffness and a third portion extending from the first portion to the second portion along side edges of the pressure sensitive film.

Disclosed herein is an example biomass impact sensor having a pressure sensitive film having a first sensing face and a second opposite face. The sensor comprises a first mat of a first fiber having a first stiffness proximate the first sensing face, a second mat of a second fiber having a second stiffness less than the first stiffness and proximate the second opposite face and a single continuous unitary mass of resin having a first portion impregnating the first mat, impregnating the second mat and extending between the first mat and the second mat along opposite edges of the pressure sensitive film to envelop the film along the opposite edges. For purposes of this disclosure, a "resin" comprises a solid or highly viscous substance of plant or synthetic origin that may, in some instances, be in the form of a polymer.

In one implementation, the single continuous unitary mass of resin completely encapsulates all sides and faces of the pressure sensitive film while impregnating the first and second mats. In one implementation, the first fiber mat comprises a first higher stiffness fiber, such as a carbon fiber, while the second fiber mat comprises a lower stiffness fiber, such as glass fibers. In one up limitation, the resin may comprise a single resin or a composition of multiple resins selected from a group of resins including, but not limited to, thermosets and thermoplastics, such as epoxies, vinylesters, polyesters, and polyamides.

In one implementation, the sensor may be manufactured and fabricated at a lower cost and with less complexity. For example, in one implementation, the pressure sensitive film may be laid upon him, rested upon or stacked upon one of the two mats, such as upon the lower stiffness mat, wherein the other of the two mats, such as the higher stiffness mat, may be stacked upon, laid upon or rested upon the pressure sensitive film. The stack may omit adhesives or welds. In other implementations, adhesives, welds or fasteners may be used to further connect the mats with one another or with the pressure sensitive film. The stack is then subjected to an encapsulating mass of the resin, while the resin is in a liquid or semi liquid state such the resin flows through and impregnates the avoids between the individual fibers of the two fiber mats, wherein the resin is subsequently allowed to harden or further solidify. The resin may continuously extend alongside the pressure sensitive film between the two mats to envelope the pressure sensitive film on at least two opposite sides and, in one implementation, to fully encapsulate the pressure sensitive film on all sides and faces.

Disclosed herein is an example harvester. The harvester a crop may comprise a gathering portion to separate crops from a growing medium, structures defining a pathway extending from the crop gathering portion and through which at least a portion of the crop is directed and a sensor along the pathway having a sensing face impacted by the portion of the crop. The sensor may comprise a pressure sensitive film having a first sensing face and a second opposite face and a conformal encasement enveloping the pressure sensitive film so as to directly abut the first sensing face and the second opposite face. The conformal encasement may comprise a first portion adjacent the first sensing face having a first stiffness, a second portion adjacent the second opposite face having a second stiffness less than the first stiffness and a third portion extending from the first portion to the second portion along side edges of the pressure sensitive film.

Disclosed herein is an example harvester that may comprise a gathering portion to separate crops from a growing medium, structures defining a pathway extending from the crop gathering portion and through which at least a portion of the crop is directed and a sensor along the pathway having a sensing face impacted by the portion of the crop. The sensor may comprise pressure sensitive film having a first sensing face and a second opposite face. The sensor comprises a first mat of a first fiber having a first stiffness proximate the first sensing face, a second mat of a second fiber having a second stiffness less than the first stiffness and proximate the second opposite face and a single continuous unitary mass of resin having a first portion impregnating the first mat, impregnating the second mat and extending between the first mat and the second mat along opposite edges of the pressure sensitive film to envelop the film along the opposite edges.

Figure 2:
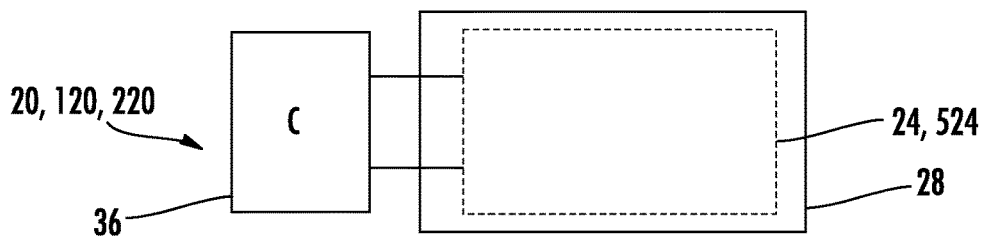
FIG. 2 is a front view of the example biomass impact sensor of capping and 1, as well as FIGS. 3, 4 and 5.

FIGS. 1 and 2 illustrate an example biomass impact sensor 20 for sensing impacts of biomass material, such as grain, material other than grain, weed seed and the like. Biomass impact sensor 20 may have a variety of sizes, shapes and configurations, not necessarily being limited to a rectangular polygon will shape. Biomass impact sensor 20 may be employed in various environments and applications such as in food processing equipment, and agricultural equipment, such as harvesters and planters. Biomass impact sensor 20 provides accurate detection of the presence, volume, mass or quantity of biomass based upon impact of the biomass with a sensing face of the sensor. Biomass impact sensor 20 provides a self-contained and durable sensing package that may be employed in rough, dirty and harsh environments including airborne debris and dust. Biomass impact sensor 20 is well-suited for use in combine harvesters for sensing grain yield and/or grain loss. Biomass impact sensor 20 comprises pressure sensitive film 24, first or front layer 28, second or rear layer 32 and controller 36.

Pressure sensitive film 24 comprises a layer or a set of stacked layers that are sensitive to pressure such that film 24 outputs signals, such as electrical signals that vary depending upon the force, density and/or frequency of impacts of such biomass material with a front sensing face 26 of film 24. Such electrical signals output by pressure sensitive film 24 are communicated in a wired or wireless fashion to controller 36. Pressure sensitive film is sandwiched between layers 28 and 32. Although pressure sensitive film 24 is illustrated as having an area less than that of layers 28 and 32, in other implementations, film 24 may have an area coextensive with the area of layers 28 and/or 32.

Front layer 28 and rear layer 32 cooperates to form a conformal encasement 33 that surrounds all faces and sides of film 24 while conforming to the shape of film 24 so as to abut and support both opposite faces 26, 27 of film 24. Front layer 28 comprise a layer of a first material composition directly abutting the sensing face 26 of film 24. Layer 28 has a first composite stiffness. In one implementation, layer 28 has a stiffness of at least 50 GPa and no greater than 75 GPa in the X-Z plane. In one implementation, layer 28 has a thickness of no greater than 1.2 mm. In one implementation, layer 28 comprises carbon fiber particles embedded within a matrix, such as a resin matrix. In one implementation, layer 28 comprises a three-dimensional grid or mat of carbon fibers having intervening voids impregnated or filled with a resin such as thermosets and thermoplastics, such as epoxies, vinylesters, polyesters, and polyamides.

Second layer 32 comprises a layer of a second material composition directly abutting the second opposite face 27 of film 24. Second layer 32 has a second composite stiffness less than the first stiffness of layer 28 in the Y-axis direction. In one implementation, layer 32 has a stiffness of at least 50 GPa and no greater than 75 GPa in the X-Z plane. In one implementation, layer 32 has a thickness of at least twice the thickness of the layer 28 in those portions directly opposite to the opposite faces 26, 27 of film 24. In one implementation, layer 32 has a thickness of at least 2 mm. In one implementation, layer 32 comprises glass fiber particles embedded within a matrix, such as a resin matrix. In one implementation, layer 32 comprises a three-dimensional grid or mat of glass fibers having intervening voids impregnated or filled with a resin, such as thermosets and thermoplastics, such as epoxies, vinylesters, polyesters, and polyamides. The greater degree of flexibility in the greater thickness of layer 32 facilitate the absorption of impact forces after such forces have been sensed by film 24, cushioning film 24.

As shown by FIG. 1, layers 28 and 32 directly abut opposite faces 26, 27 of film 24 while being joined or abutting one another along opposite edges of film 24 to envelop film 24 on the opposite edges. In the example illustrated, layers 28 and 32 are joined to one another or directly abut one another along a seam 40 that is generally flush or coextensive with the plane of the sensing face 26 of film 24. In such an implementation, pressure sensitive film 24 is inset within a recess 38 formed in layer 32, wherein layer 28 serves as a cover or cap, resting upon and directly abutting sensing face 26 of film 24. In such an implementation, the direct contact between layer 28 and film 26 facilitates the transmission of impact forces to pressure sensitive film 24. At the same time, layer 28 is firmly supported by layer 32 and at least partially envelops or, in some implementations, fully encapsulates film 24 to protect film 24 from contamination or damaging shocks.

In one implementation, film 24 may be pressed into layer 32 while layer 32 is in an at least partially malleable or liquid state. In other implementations, recess 38 may be preformed within layer 32, wherein film 24 is inserted into recess 38.

Controller 36 comprises a processor and a non-transitory computer-readable medium containing instructions for directing the processor to receive biomass impact signals from film 24 and to determine biomass flow rate, yield, volume, density or mass based upon such impact signals. For example, based upon such signals, controller 36 may consult a lookup table with empirically determined data correlating impact values to grain yield, grain loss, material other than grain (MOG) yield, material other than grain loss, weed presence or volume and the like. Such grain yield, grain loss, MOG yield, weed yield/presence of the like may be further utilized by controller 36 to generate and store field maps for future crop management decisions and/or to automatically adjust operational parameters of a machine that is harvesting, transferring or processing the biomass material, such as a crop in the form of grain or MOG.

Figure 3:
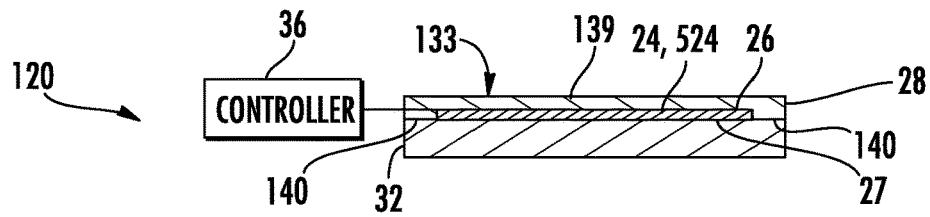
FIG. 3 is a sectional view of an example biomass impact sensor.

FIGS. 2 and 3 illustrate an example biomass impact sensor 120. Sensor 120 is similar to sensor 20 described above except that layers 28 and 32 form a slightly different conformal encasement 133 having a differently located seam between the layers. As shown by FIG. 3, pressure sensitive film 24 is embedded into or is recessed within layer 28 such that layers 28 and 32 abut one another along a seam 140 that is flush with or coextensive with the plane of the face 27 of film 24. Those remaining components or elements of sensor 120 which correspond to components of sensor 20 are numbered similarly. In one implementation, layer 28 may be formed over film 26 while film 28 is in an at least partially malleable or liquid state. In other implementations, a recess 139 may be pre-formed within layer 28, wherein layer 26 is inserted into recess 139.

Figure 4:
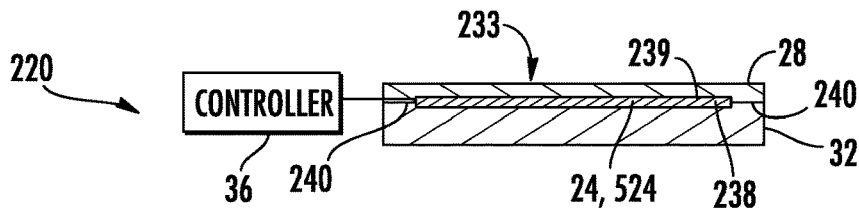
FIG. 4 is a sectional view of an example biomass impact sensor.

FIGS. 2 and 4 illustrate an example biomass impact sensor 220. Sensor 220 is similar to sensor 20 described above except that layers 28 and 32 form a slightly different conformal encasement 233 having a differently located seam between the layers. As shown by FIG. 4, pressure sensitive film 24 is embedded into or is recessed into each of layers 28, 32 such that layers 28 and 32 abut one another along a seam 240 that extends in a plane that is between the plane of faces 26 and 27 of film 24. Those remaining components or elements of sensor 220 which correspond to components of sensor 20 are numbered similarly. In one implementation, layers 28 and 32 may be formed over and under film 24 while layers 28 and 32 are each in an at least partially malleable or liquid state. In other implementations, a recess 238 may be pre-formed within layer 28 and a recess 239 may be formed in layer 32, wherein film 24 is inserted into recesses 238 and 239. In yet another implementation, a recess may be preformed in one of layers 28, 32, wherein film 24 is inserted into the recess and the other of layer 28, 32, while in an at least partial liquid or malleable state, is formed over in about the portion of film 24 projecting from the recess.

Figure 5:
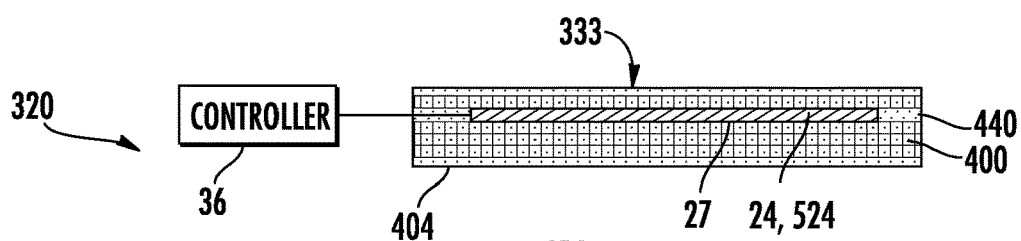
FIG. 5 is a sectional view of an example biomass impact sensor.

FIGS. 2 and 5 illustrate an example biomass impact sensor 320. Biomass impact sensor 320 comprises pressure sensitive film 24 (described above), a single integral unitary body conformal encasement 333 and controller 36 (described above). Conformal encasement 333 completely surrounds and encases or encapsulates pressure sensitive film 24 on all sides. In the example illustrated, conformal encasement 333 is in contact with and abuts all edges and all faces of film 24, fully supporting and securely retaining film 24 in place. Pressure sensitive film 24 is in communication with controller 36 via a wired or wireless connection. In the example illustrated, the connection is a wired connection with electrical wires, traces or leads extending through and from encasement 333 into connection with controller 36.

Conformal encasement 333 comprises stiffening grid or mat 400, stiffening mat or grid 402 and resin mass 404. Stiffening grid or mat 400 comprises an open celled structure underlying and directly contacting face 27 of film 24. Mat 400 is formed from a material composition and/or architecture having a first stiffness in a Y-axis direction, perpendicular to face 26 of film 24. The first stiffness is such that mat 400 serves as a shock absorber, absorbing forces transmitted through sensor 320. In one implementation, mat 400 comprises a glass fiber mat. In other implementations, mat 400 may be formed from other fibers or non-fibrous materials.

Stiffening grid or mat 402 comprises an open celled structure overlying and stacked directly upon face 26 of film 24. Mat is formed from a material composition and/or architecture having a second stiffness greater than the first stiffness. The greater degree of stiffness provided by mat 402 facilitates the transmission of impact forces from biomass material (such as grain, particles or other biomass materials) to the sensing face 26 of film 24. In one implementation, mat 402 is formed from material different than that of mat 400 to provide mat 402 with a greater degree of stiffness in the Y-axis direction. In another implementation, mat 402 is formed from a same material as that of mat 400, but wherein mat 402 has a different architecture are geometry so as to have a greater degree of stiffness in the Y-axis direction. For example, mat 402 may have a more dense lattice structure or a different lattice geometry of cells and walls that offer a greater degree of strength or stiffness, resistance to bending or deflection. In yet other implementations, mat 402 may have a different lattice structure are geometry and may be formed from a different material such that mat 402 has a greater degree of stiffness. In one implementation, mat 402 is formed from a carbon fiber.

Resin mass 404 comprises an amorphous mass of resin, such as thermosets and thermoplastics, such as epoxies, vinylesters, polyesters, and polyamides, completely surrounding and encasing film 24. Resin mass 404 impregnates or fills in the voids or interstices of the open cell grid or mats 400, 402 will also extending between such mats 400, 402 along all of the opposing side edges of film 24. In some implementations, resin mass 404 forms a body that seals film 24 in place. Resin mass 404 extends along and beyond side edges of film 24. Resin mass 404 cooperates with mat 400 to form a first portion of encasement 333 having a first degree of stiffness and cooperates with mat 402 to form a second portion of encasement 333 having a second degree of stiffness greater than the first degree of stiffness.

Figure 6:
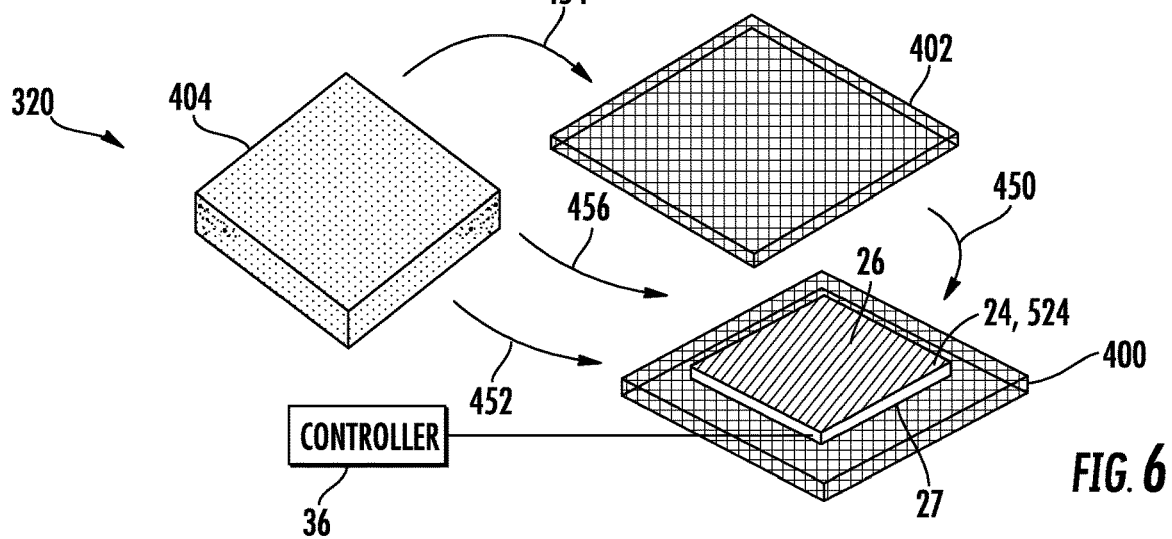
FIG. 6 is an exploded perspective view of the example biomass impact sensor of FIG. 5.

FIG. 6 is an exploded perspective view illustrating one example method of forming sensor 320. As shown in FIG. 6, film 24 is laid directly upon or stacked upon mat 400. As indicated by arrow 450 in FIG. 6, mat 402 is then laid directly upon or stacked upon film 24. This "sandwich" is in subjected to an infusion of resin mass 404. During such infusion, the resin mass 404 is in a viscous or flowable state. As indicated by arrow 452, the resin mass 404 impregnates and flows through the voids or interstices of mat 400 to fill such voids. As indicated by arrow 454, the resin mass 404 impregnates and flows through the voids or interstices of mat 402 to fill such voids. As indicated by arrow 456, the resin mass 404 fills in the gaps or spaces between the mats 400, 402 along the side edges of film 24 to form a connecting portion 440 (shown in FIG. 5), of just the resin, between mats 400, 402 along the side edges of film 24. The result is a single continuous integral unitary body of resin mass 404 about film 24. After such infusing or impregnating, resin mass 404 is allowed to cool and/or cure so as to solidify. As should be appreciated, the forming of resin mass 404 about mats 400, 402 and film 24 may occur in a mold or other similar structure.

Figure 7:
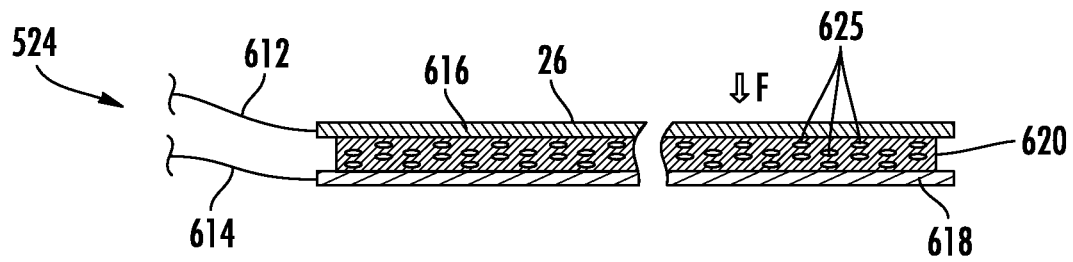
FIG. 7 is a sectional view of an example pressure sensitive film that may be utilized in the sensors of FIGS. 1-5.
Figure 8:
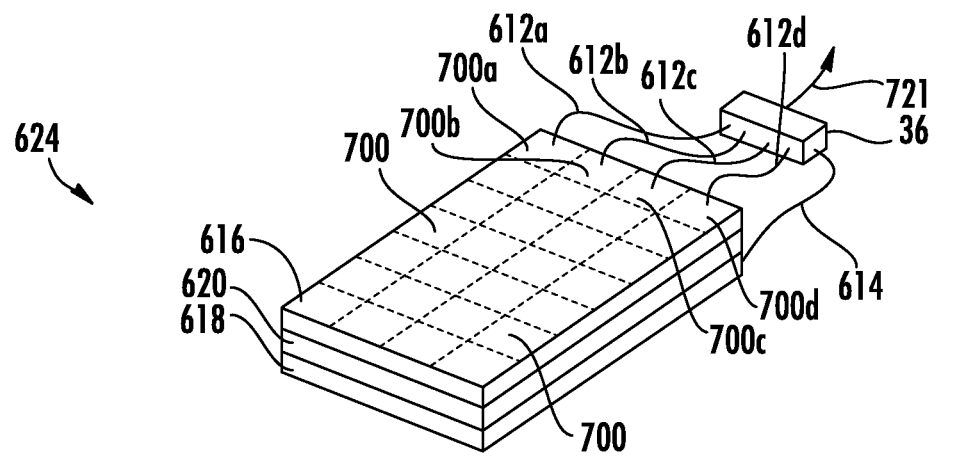
FIG. 8 is a front perspective view of another example pressure sensitive film that may be utilized in the sensors of FIGS. 1-5.

FIGS. 7 and 8 illustrate an example pressure sensitive film 524, one example of pressure sensitive film 24 shown in FIGS. 1-6. In other implementations, the pressure sensitive film 24 shown in FIGS. 1-6 may comprise other forms of a pressure sensitive film. The example pressure sensitive film 524 corresponds to the impact sensor 301 described in co-pending U.S. patent application Ser. No. 14/794,089 filed on Jul. 8, 2015 by Bischoff et al., the full disclosure of which is hereby incorporated by reference. In this example, the pressure sensitive film 524 has an upper conductive layer 616, a lower conductive layer 618, and an impact responsive layer 620.

The upper conductive layer 616 conducts electricity to or from one surface of the impact responsive layer 620 to the electrical connection 612. The lower conductive layer 618 conducts electricity to or from an opposing surface of the impact responsive layer 620 to the electrical connection 614.

The impact responsive layer 620 comprises a pressure responsive media that changes its electrical characteristics upon the impact of a seed or other biomass material. The electrical characteristics may comprise a change in resistivity, a change in capacitance, or a production of electricity caused by the impact of the biomass material. These electrical characteristics are changed locally in the impact responsive layer 620 immediately adjacent to the location of the biomass impact. Typical pressure responsive media includes such things as electromechanical films, cellular polymers, polymer electrets, piezoelectric polymers, piezoelectric films, and quasi-piezoelectric films.

In one particular arrangement, the impact responsive layer 620 comprises a cellular polymer sensing media. This material is formed as a thin polypropylene sheet having a cellular structure. This material is manufactured by stretching a polypropylene preform in longitudinal and transverse directions. The stretched sheet is then charged by a corona discharge method. The stretched sheet is full tiny gas voids or "cells" 625 extending in a longitudinal and transverse direction. These cells are separated from one another by leaf-like polypropylene layers. The cells can be compared to large electrical dipoles that are easily compressed in a thickness direction by an externally applied force. The change in thickness at the site of the compression (in our case, the impact site of the biomass) modifies the dimensions of the dipoles which generates a corresponding electrical charge.

The biaxial stretching and cellular nature of the material causes the cellular polymer media to respond to compression of the media in a direction normal to the planar extent of the media. Advantageously, it also causes the media to be relatively nonresponsive to shear forces applied to the surface of the media. In fact, cellular polymer sensing media can have a 100-fold reduced sensitivity to shearing forces (i.e. sliding contact) as opposed to normal forces (i.e. particle impacts normal to the surface of the media).

This is of particular benefit for grain loss sensors that are disposed normal to a path of incoming, falling grain or other particulate matter. Grain (or other particulate matter) impacting the surface of the sensor normal to the longitudinal and transverse extent of the impact responsive layer will generate a strong signal upon initial (normal) impact. As those same particles slide down the face of the sensor after impact, the shear forces generated by the sliding of the particles will generate a corresponding electric charge which is greatly reduced. This will innately reduce or eliminate the signals generated from second impacts and sliding movement of the particulate matter after the initial impact. In this manner, double (or triple) counts of each biomass impact can be reduced or eliminated and therefore the number of particles contacting the sensor can be more accurately counted.

In another arrangement, the impact responsive layer 320 comprises a polar piezoelectric polymer (e.g. polyvinylidenefluoride or PVDF) that generates an electrical charge upon impact.

In another arrangement the impact responsive layer 620 comprises a material that changes its electrical resistance upon impact and compression, such as molybdenum disulfide-based inks, or conductive coating products such as the "Cho-Shield" line produced by Parker-Chomerics of Woburn, Mass.

In another arrangement, the impact responsive layer 620 comprises polymer composites that further comprise polymers (e.g. polymers with polarizable moieties such as polyimides, polyamides, silicon-based polymers, vinyl polymers, polyurethanes, polyureas, polythioureas, polyacrylates, polyesters and/or biopolymers) to which carbon nanotubes (e.g. single wall nanotubes and multiwall nanotubes) have been added, or to which electroceramic particles (e.g. lead-zirconium titanate, lanthanum-modified lead-zirconate titanate, niobium-modified lead-zirconate titanate and/or barium titanate) or to which both have been added. See, for example, published patent application US2006/0084752 A1, which is incorporated herein by reference for all that it teaches.

In one arrangement, the upper conductive layer 616 and the lower conductive layer 618 may comprise a film base (e.g. a polyimide (e.g.Kapton), BiPEt (e.g. Mylar, Melinex, Hostaphan), polyester or PTFE (polytetrafluoroethylene) (e.g. Teflon) to which a conductive media (e.g. metals such as aluminum, silver, or gold; or conductive oxides such asindium tin oxide; or carbon such as carbon nanotubes or graphene) is deposited by a sputter-, vapor- or plasma-deposition process (with or without post-deposition annealing or curing). In this arrangement, a surface of the upper conductive layer 616 in the lower conductive layer 618 to which the conductive media is applied is then bonded to the impact responsive layer 620. This arrangement has the benefit of providing an outwardly facing (e.g. the sensing face 26) polymer layer that provides strength, flexibility, and durability, yet covers and protects a more fragile conductive media.

In one arrangement, the upper conductive layer 616 and the lower conductive layer 618 are continuous and homogeneous over substantially the entire surface of the impact responsive layer. This is particularly beneficial when used to detect random impacts of particulate matter. In the present case (i.e. that of a grain impact sensor) the particular matter impacts random locations on the surface of the sensor. Grain falls from the threshing and separating section of a combine in essentially a random pattern over the surface of the grain impact sensor. It is not directed to a particular region of the grain impact sensor. Each particle has its own random and unpredictable velocity and location as it falls into the surface of the grain impact sensor. As a result, there is no way all you got let members of the liberal left to predict the point of impact of any particle.

To accommodate this virtually infinite number of impact locations, substantially the entire surface of the pressure sensitive film is preferably equally responsive to impacts of particles. Thus, the upper conductive layer 616 and the lower conductive layer 618 preferably do not vary in their conductive characteristics over the entire surface of the grain impact sensor. If grain impact occurs at a random location (X, Y) on grain impact sensor and an identical grain impact occurs at a location even as little as 1 mm away from the location (X, Y), an identical electrical change (e.g. a change in resistivity, capacitance, or electrical charge) should be generated by the impact responsive layer 620 and that identical electrical change should be identically communicated through the upper conductive layer 616 in the lower conductive layer 618 to a signal processing circuit. The conveyance of this identical electrical change through the upper conductive layer 616 and the lower conductive layer 618 is enhanced by the continuous and homogeneous characteristics of the upper conductive layer 616 and the lower conductive layer 618 over substantially the entire surface of the grain impact sensor.

The thickness of the upper conductive layer 616 and the lower conductive layer 618 is generally between 7 and 25 micrometres. "Dynamic mass" as used herein refers to the mass of the sensor that is moved in order to cause an electrical change sufficient to indicate a grain impact. "Dynamic volume" as used herein refers to the volume of the sensor that is moved in order to cause an electrical change sufficient to indicate a grain impact.

The "biomass-to-sensor mass ratio" as used herein refers to the mass of a biomass making an impact divided by the dynamic mass of the sensor that responds to that impact. As the biomass-to-sensor mass ratio decreases, the natural frequency of the sensor decreases making it hard to identify individual biomass impacts upon the sensor surface. Further, the larger, thinner and more flexible the particulate impact sensor is made, the more modes of vibration are generated in the particulate matter impact sensor, each mode having its own natural frequencies of oscillation, which also makes it difficult to identify an individual biomass impact from the signal generated by the particulate matter impact sensor.

The dynamic mass of the pressure sensitive film 524 is less than the mass of the biomass particles whose impacts are being sensed by the film. A corn seed has a mass of about 1000 mg, a soybean seed has a mass of about 800 mg, a barley seed has a mass of about 75 mg, and wheat seed has a mass of about 60 mg. These seeds are rounded, generally spherical, ovoid, or oblate, and have an overall size of 4 mm to 10 mm.

Depending upon the resilience of the 524 and the size and mass of the biomass particle, a typical particle may impact and deflect and/or compress a small surface area (2 mm$^2$ to 10 mm$^2$) of the pressure sensitive film 524 to a depth typically ranging between 25 and 250 micrometers. The depth of this depression depends upon the thickness of the film 524, the thickness of any protective film layer of that may be provided in front of the sensing film 524, and the thickness of any intermediate layer (not shown) that may be disposed between the film 524 and any support layer.

The mass density of the pressure sensitive film 524 may be approximated as 1.3 g/cm 3.

In one example, assume that the sensing media layer is impacted by the biomass particle and is compressed only slightly, e.g. to a depth of 25 micrometres, and that this compression occurs over of surface area of 2 mm$^2$, the dynamic mass of the film 524 is approximately 17 micrograms. Assuming that the biomass particulate is a corn kernel having a mass of 1 g, this arrangement provides a biomass-to-sensor mass ratio of 1 g/17 micrograms or approximately 60,000.

In another example, assume that the sensing media layer is impacted by the biomass particle and is compressed significantly more, e.g. to a depth of 250 micrometres over a 10 mm$^2$ surface area. In this case, the dynamic mass of the film 524 is approximately 850 micrograms. Assuming that biomass particle is a corn kernel having a mass of 1 g, this arrangement provides a biomass-to-sensor mass ratio of 1 g/850 micrograms or approximately 1200.

To provide optimum performance, the pressure sensitive film 524 has a biomass-to-sensor mass ratio greater than 5, alternatively greater than 50, alternatively greater than 500 and alternatively greater than 5000.

FIG. 8 is a top perspective view of pressure sensitive film 624, a first alternative construction of the particulate pressure sensitive film 524. As with film 524, film 624 may be incorporated into any of the aforementioned or following biomass impact sensors. In film 624, the upper conductive layer 616 is divided into a plurality of separate, electrically discontinuous, regions 700 (shown in FIG. 8 as 700, 700a, 700b, et seq.).

The boundaries of each of the electrically discontinuous regions (i.e. electrodes) 700 are illustrated in FIG. 8 as dashed lines. In FIG. 8, there are 28 of these regions. The regions are discontinuous in a lateral direction "L" and in a direction "0" that is orthogonal to the lateral direction "L".

The lateral direction "L" is oriented perpendicular to the direction of travel of the agricultural combine on which the particulate matter impact sensor 301 is mounted. By providing multiple regions 700 of the film 624 that are oriented adjacent to each other in the direction "L", the film 524 is capable of sensing the lateral distribution of biomass impacts (i.e. side-to-side).

Each of the regions 700 of the upper conductive layer 716 has a corresponding electrical connection 712 that is connected to a signal processing circuit in the form of controller 36. For convenience of illustration, only four of these electrical connections 612 are shown (612a, 612b, 612c, and 612d). The other regions 700 are similarly connected to the controller 36.

The lower conductive layer 618 extends, unbroken, across the entire lower surface of the impact responsive layer, and thus provides a common electrical connection to the lower surface of the impact responsive layer 620 for each of the individual regions 700 (700a, 700b, etc.).

The controller 36 is configured to receive the electrical changes (discussed above) separately from each of these regions 700 as they are generated by the impact responsive layer 620. In this manner, the electrical change generated by an impact upon the surface of the film 524 registers on the particular corresponding upper electrical connection (612a, 612b, etc.) and on the common electrical connection 614. The controller 36 is configured to determine the location of the impact based upon which of the electrical connections 612 (612a, 612b, etc.) generates a signal. The controller 36 is further configured to generate an output signal on signal line 721 that indicates not only the occurrence of an impact, but also the particular region 700 (700a, 700b, etc.) of the regions 700 where the impact occurred. In this manner, the controller 36 is configured to determine not only (i) the occurrence of an impact, but (ii) the relative e.g. x,y) location of the impact on the film 524.

In a second alternative arrangement similar to that of the arrangement in FIG. 8, the lower conductive layer 618 is configured as the upper conductive layer 616 is in FIG. 8, and the upper conductive layer 616 is configured as the lower conductive layer 618 is in FIG. 8. In other words, the sensing media layer 600 is reversed (compared to that in FIG. 8) such that the lower conductive layer 618 is divided into regions 700 with each region 700 having its own, separate electrical connection 614 to the controller 36 and with a single electrical connection 614 extending across the entire top surface of the film 524. This second alternative arrangement has the advantage of providing a substantially continuous and unbroken upper conductive layer 616, which is more resistant to repeated impacts of particles on the first surface as compared to the first alternative arrangement shown in FIG. 8. Wherever there are discontinuities in the upper conductive layer 616 (such as gaps between individual regions 700) it is possible that the upper conductive layer 616 will delaminate from the impact responsive layer 620.

In a third alternative arrangement similar to that of the arrangement in FIGS. 7 and 8, both the lower conductive layer 618 and the upper conductive layer 616 are divided into regions 700. To sense electrical changes due to particulate matter impacts in a particular region 700 of the film 524, individual electrical connections 612, 614, both upper and lower, to each region 700 are provided. Thus, for each region 700, an electrical connection 612 connecting to the upper surface and electrical connection 614 connected to the lower surface of that region, and that region alone, is provided for each of the regions 700 of the particulate matter impact sensor 601 and are connected to the signal processing circuitry of controller 36.

The individual regions 700 of the upper conductive layer 616 and/or the lower conductive layer 618 for any of these three alternative arrangements can be provided in a variety of ways. In a first process, the film 524 can be formed as shown in FIG. 7, with a continuous upper conductive layer 616 and a continuous lower conductive layer 618 that are bonded to the impact responsive layer 620. These continuous layers can then be divided into independent regions 700 by removing the conductive material from between each adjacent region 700. This removal would follow (for example) the dashed lines shown in FIG. 8. In this manner, the upper conductive layer 616, the lower conductive layer 618, or both of the conductive layers can be segmented into separate regions 700. This can be done, for example, by a laser emitting a computer steerable laser beam that mark the divisions between individual regions 700. This first process has the advantage of permitting the manufacture of a standard, uniform, and large web of material having an upper conductive layer 616, a lower conductive layer 618, and an impact responsive layer 620, and then permitting it to be cut to reduced dimensions that fit particular film 524, then dividing either (or both) of the upper conductive layer 616 and the lower conductive layer 618 into custom regions 700 for a particular application.

In a second process, the impact responsive layer 620 can be provided, and the upper conductive layer 616 and the lower conductive layer 618 (or both) can be applied as a coating on the impact responsive layer 620 in the form of separate regions 700. This coating can be done, for example, by screen-printing of conductive materials such as conductive inks, vapor deposition of conductive material (e.g. conductive oxides such as indium tin oxide or carbon such as graphene), or plasma spray deposition of conductive material (e.g. conductive oxides or carbon).

If in the second process the coatings cannot be selectively applied as separate regions 700 to the impact responsive layer 620, then a screen, mask, or stencil can be disposed between the source of the conductive material and the impact responsive layer 620 itself during the coating process to ensure that separate regions 700 are produced on the surface of the impact responsive layer 620. In other words, that non-coated, non-conductive regions are provided (for example) where the dashed lines appear in FIG. 8 by the interposition of the screen, mask, or stencil between the source of the coating and the impact responsive layer 620.

In a third process, the upper conductive layer 616, the lower conductive layer 618, or both (depending upon the desired configuration) are provided as a continuous conductive layer on an inner surface of a film base (as described above) and then selectively removed from the film base using the first process to thereby define the regions 700. This film base (with regions 700 defined thereon) can then be fixed to the impact responsive layer 620.

In a fourth process, the upper conductive layer 616 and/or the lower conductive layer 618 can be applied as individual regions 700 on a film base (as described above) either directly or with an interposed screen, mask, or stencil. This film base (with regions 700 defined thereon) can then be fixed to the impact responsive layer 620.

Figure 9:
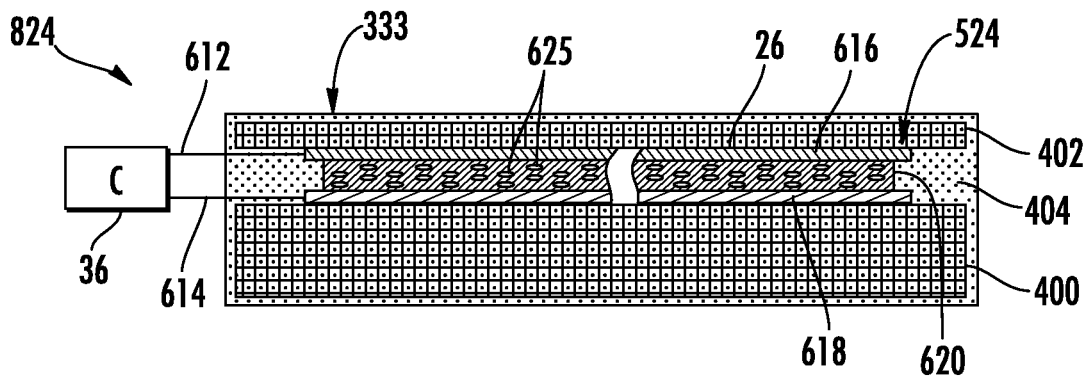
FIG. 9 is a sectional of an example biomass impact sensor incorporating the pressure sensitive film of FIG. 7.

FIG. 9 is a sectional view illustrating the above described pressure sensitive film 524 encased in the conformal encasing 333 described above to form biomass impact sensor 820. Sensor 820 is similar to sensor 320 in all respects except that sensor 824 specifically comprises film 524. As shown by FIG. 9, film 524 is sandwiched between mat's 400, 402, directly resting upon mat 400 in contact with mat 400 and directly underlying mat 402 in contact with mat 402. This "sandwich" is in covered, filled, impregnated and infused with resin mass 404. In one up limitation, the electrically conductive leads 612 and 614 are connected to film 524 and then, themselves, encapsulated by the subsequently applied resin mass 404. The resin mass 404 is subsequently allowed to cool and/or cure to a solid or solidified state. The resin mass 404 seals and completely encapsulates film 524, retaining film 524 in place against the upper portion of encasement 333 including mat 402 and the lower or rear portion of encasement 333 including mat 400. Such secure positional retention is achieved without the use of adhesives, welds or fasteners. In other implementations, film 524 may additionally or alternatively be held and retained in place by adhesive, welds or fasteners.

Figure 10:
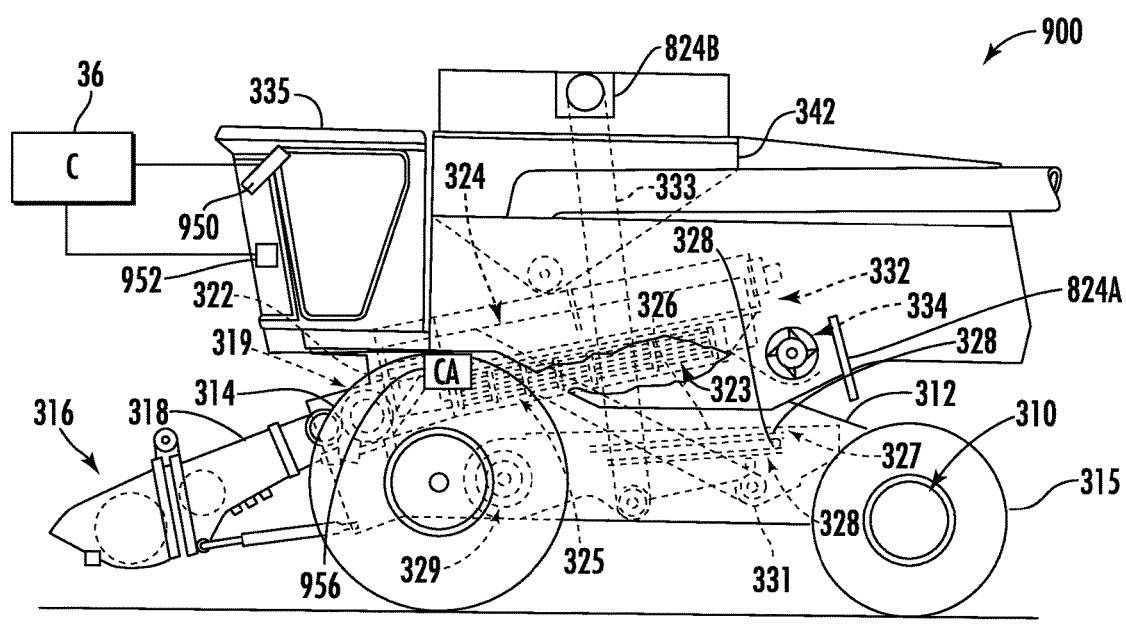
FIG. 10 is a side view of an example harvester including the biomass impact sensors of FIG. 9.

FIG. 10 is a side view of an example harvester 900 (with internal portion shown in broken lines) incorporating biomass impact sensor 824 at different locations. In the example illustrated, harvester 900 comprises a first biomass impact sensor 824 serving as a grain loss sensor and a second biomass impact sensor 824B serving as a grain yield sensor. In other implementations, harvester 900 may include biomass impact sensor 824 at other locations. Although biomass impact sensors 824 are illustrated as being utilized with combine harvester 900, biomass impact sensors 824 may likewise be utilized in other types of harvesters, with food or other devices.

In addition to biomass impact sensors 824A and 824B, which are each potentially similar to biomass impact sensor 824 described above, harvester 900 comprises a main frame 912 having wheel structure including front and rear ground engaging wheels 914 and 915 supporting the main frame for forward movement over a field of crop to be harvested. The front wheels 914 are driven by an electronically controlled hydrostatic transmission.

As further shown by FIG. 10, harvester 900 further comprises a vertically adjustable header or harvesting platform 916 that is used for harvesting a crop and directing it to a feeder house 918. The feeder house 318 is pivotally connected to the frame 912 and includes a conveyor for conveying the harvested crop to a beater 919. The beater 919 directs the crop upwardly through an inlet transition section 922 to a rotary cleaning and separating assembly 924. In other implementations, other orientations and types of cleaning structures and other types of headers 916, such as transverse frame supporting individual row units, are utilized.

The rotary cleaning and separating assembly 924 threshes and separates the harvested crop material. Grain and chaff fall through a concave 925 and separation grates 923 on the bottom of the assembly 924 to a cleaning system 926, and are cleaned by a chaffer 927, sieve 928 and air fan 929. The cleaning system 926 removes the chaff and directs the clean grain to elevator 933. Clean grain elevator 933 conveys the grain to tank 942. The clean grain in the tank 942 can be unloaded into a grain cart or truck by unloading auger. Tailings fall into the return elevator or auger 931 and are conveyed to the rotor 937 where they are threshed a second time.

Threshed and separated straw is discharged from the rotary cleaning and separating assembly 924 through an outlet 932 to a discharge beater 934. The discharge beater 934, in turn, propels the straw out the rear of the combine. It should be noted that the discharge beater 934 could also discharge crop material other than grain directly to a straw chopper. The operation of the combine is controlled from an operator's cab 935.

As further shown by FIG. 10, biomass impact sensor 824A is situated or supported the harvester 900 rearward of discharge beater 934 such that the stream of biomass material exiting the rear of harvester 900 first impacts sensor 824A. This stream may include both grain and MOG. In response to impacts of the stream against sensor 824A, sensor 824A output electrical signals which are transmitted to controller 36. Such signals are processed by controller 36 to indicate a degree of grain loss, a percentage, mass, flow rate or the like of grain (as compared to MOG) exiting the rear of harvester 900. Controller 36 may output such grain loss determinations to a display 950 for viewing by an operator, wherein the operator can implement changes to the operational parameters of harvester 900 and an attempt to reduce such grain losses. In a different implementation or when harvester 900 is operating in an automated mode, controller 36 may output such grain loss determinations to a harvester controller 952 which may automatically adjust operational parameters of harvester 900 in an attempt to mitigate grain losses. For example, in one implementation, controller 952, using the signals received from controller 36, may output control signals causing a grate or concave actuator 956 (such as a hydraulic or pneumatic cylinder-piston assembly, an electric solenoid or other mechanical repositioning mechanism) to adjust a setting associated with the concave 925, such as this spacing relative to the grates. In yet another implementation, controller 952, using the signals received from controller 36, outputs control signals adjusting the rotational speed of the rotor 937 of harvester 900. In still other implementations, controller 952 may adjust other operational parameters of harvester 900, such as the speed at which it is traversing a field, or the operational parameters of chaffer 927 or sieve 928. In some implementations, controller 952 may additionally or alternatively recorder store grain loss information and generate a grain loss map, correlating determined grain loss values with geo-positions of the harvester 900 as it traverses the field, such as determined through the use of satellite global positioning system data received by controller 952 of harvester 900.

Biomass impact sensor 824B is similar to biomass impact sensor 824A except the biomass impact sensor 824B is supported by harvester 900 so as to intercept a stream of grain being conveyed on his way to grain tank 942. The stream of grain being conveyed towards grain tank 942 impacts sensor 824B. In response to impacts of the stream against sensor 824B, sensor 824B outputs electrical signals which are transmitted to controller 36. Such signals are processed by controller 36 to indicate a current ongoing grain yield estimate. Controller 36 may output such grain yield values to display 950 for viewing by an operator, wherein the operator can implement changes to the operational parameters of harvester 900 and an attempt to reduce such grain losses or accommodate variations in yield. In a different implementations, or when harvester 900 is operating in an automated mode, controller 36 may output such grain yield determinations to a harvester controller 952 which may automatically adjust operational parameters of harvester 900 in an attempt to accommodate fluctuations in ongoing, real time grain yield. For example, in one implementation, controller 952, using the signals received from controller 36, may output control signals causing a grate or concave actuator 956 to adjust a setting associated with the concave 925, such as this spacing relative to the grates. In yet another implementation, controller 952, using the signals received from controller 36, outputs control signals adjusting the rotational speed of the rotor 937 of harvester 900. In still other implementations, controller 952 may adjust other operational parameters of harvester 900, such as the speed at which it is traversing a field, or the operational parameters of chaffer 927 or sieve 928. In some implementations, controller 952 may additionally or alternatively record or store grain yield information and generate a grain yield map, correlating determined grain yield values with geo-positions of the harvester 900 as it traverses the field, such as determined through the use of satellite global positioning system data received by controller 952 of harvester 900.

Although the present disclosure has been described with reference to example implementations, workers skilled in the art will recognize that changes may be made in form and detail without departing from the spirit and scope of the claimed subject matter. For example, although different example implementations may have been described as including features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A biomass impact sensor for sensing impacts of biomass material, the sensor comprising:
   a pressure sensitive film having a first sensing face and a second opposite face;
   a conformal encasement enveloping the pressure sensitive film so as to directly abut the first sensing face and the second opposite face, the conformal encasement comprising:

a first portion adjacent the first sensing face having a first stiffness;

a second portion adjacent the second opposite face having a second stiffness less than the first stiffness; and a third portion extending from the first portion to the second portion along side edges of the pressure sensitive film.

2. The biomass impact sensor of claim 1, wherein the conformal encasement comprises a first layer directly abutting the first sensing face in forming the first portion; and a second layer directly abutting the second opposite face in forming the second portion, wherein the first layer and the second layer are in abutment with one another along the side edges of the pressure sensitive film.

3. The sensor of claim 2, wherein the pressure sensitive film is captured and retained between the first layer and the second layer without adhesives therebetween.

4. The sensor of claim 1, where the first layer has a thickness of no greater than 1.2 mm.

5. The sensor of claim 4, wherein the second layer has a thickness of at least 2 mm.

6. The sensor of claim 1, wherein the second layer has a thickness of at least 2 mm.

7. The sensor of claim 1, wherein the first stiffness is at least twice the second stiffness.

8. The sensor of claim 1, wherein the first portion comprises a carbon fiber impregnated with a resin.

9. The sensor of claim 8, wherein the second portion comprises a glass fiber impregnated with the resin.

10. The sensor of claim 9, wherein the conformal encasement comprises a single unitary body formed by an integral mass of the resin which impregnates a mat of the carbon fiber in the first portion and which impregnates a mat of the glass fiber in the second portion.

11. The sensor of claim 1, wherein the pressure sensitive film comprises internal elliptical voids.

12. The sensor of claim 1, wherein the conformal encasement comprises a mass of resin completely encapsulating all external surfaces of the pressure sensitive film.

13. A biomass impact sensor comprising:

a pressure sensitive film having a first sensing face and a second opposite face;

a first mat of a first fiber having a first stiffness proximate the first sensing face;

a second mat of a second fiber having a second stiffness less than the first stiffness and proximate the second opposite face;

a single continuous unitary mass of resin having a first portion impregnating the first mat, impregnating the second mat and extending between the first mat and the second mat along opposite edges of the pressure sensitive film to envelop the film along the opposite edges.

14. The sensor of claim 13, wherein the pressure sensitive film is captured and retained between the first mat and the second mat without adhesives therebetween.

15. The sensor of claim 13, wherein the first mat impregnated with the resin has a first stiffness and wherein the second mat impregnated with resin has a stiffness no greater than one half the first stiffness.

16. The sensor of claim 13, where the first mat with the impregnated resin has a thickness of no greater than 1.2 mm.

17. The sensor of claim 16, wherein the second mat with the impregnated resin has a thickness of at least 2 mm.

18. The sensor of claim 13, wherein the second mat with the impregnated resin has a thickness of at least 2 mm.

19. The sensor of claim 13, wherein the first mat comprises carbon fibers and wherein the second mat comprises glass fibers.

20. A harvester comprising:

a crop gathering portion to separate crops from a growing medium;

structures defining a pathway extending from the crop gathering portion and through which at least a portion of the crop is directed;

a sensor along the pathway having a sensing face impacted by the portion of the crop, the sensor comprising:

a pressure sensitive film having a first sensing face and a second opposite face;

a conformal encasement enveloping the pressure sensitive film so as to directly abut the first sensing face and the second opposite face, the conformal encasement comprising:

a first portion adjacent the first sensing face having a first stiffness;

a second portion adjacent the second opposite face having a second stiffness less than the first stiffness; and a third portion extending from the first portion to the second portion along side edges of the pressure sensitive film.

\* \* \* \* \*